(12) United States Patent
Simpson et al.

(10) Patent No.: US 11,998,688 B2
(45) Date of Patent: Jun. 4, 2024

(54) NASAL MEDICATION OR DRUG DELIVERY DEVICES AND METHODS

(71) Applicant: INdev, LLC, Austin, TX (US)

(72) Inventors: Kevin Simpson, Austin, TX (US); Nicholas Norman, Charlotte, NC (US); Alan Snyder, Charleston, SC (US)

(73) Assignee: Indev, LLC, Austin, TX (US)

(*) Notice: Subject to any disclaimer, the term of this patent is extended or adjusted under 35 U.S.C. 154(b) by 683 days.

(21) Appl. No.: 16/911,096

(22) Filed: Jun. 24, 2020

(65) Prior Publication Data

US 2020/0398005 A1 Dec. 24, 2020

Related U.S. Application Data

(60) Provisional application No. 62/865,783, filed on Jun. 24, 2019.

(51) Int. Cl.
*A61M 15/08* (2006.01)
*A61M 11/00* (2006.01)
(Continued)

(52) U.S. Cl.
CPC .......... *A61M 15/08* (2013.01); *A61M 11/002* (2014.02); *A61M 11/02* (2013.01);
(Continued)

(58) Field of Classification Search
CPC .............. A61M 15/08; A61M 15/0013; A61M 15/0025; A61M 15/0035; A61M 15/0066;
(Continued)

(56) References Cited

U.S. PATENT DOCUMENTS 701,711 A * 6/1902 Goltermann
4,962,868 A  10/1990 Borchard
(Continued)

FOREIGN PATENT DOCUMENTS

EP 1728529 A1 12/2006
GB 2488735 A 9/2012
(Continued)

OTHER PUBLICATIONS

United States International Searching Authority; International Search Report & Written Opinion for PCT/US2020/039411; dated Sep. 21, 2020; 12 pages; Arlington, VA; US.
(Continued)

*Primary Examiner* — Justine R Yu
*Assistant Examiner* — Matthew R Moon
(74) *Attorney, Agent, or Firm* — Kirk Dorius; Dorius Law P.C.

(57) ABSTRACT

Nasal medication or drug delivery devices and methods for delivering adjustable or variable metered volumetric doses of medication or drugs to a nasal passageway of a user or patient. Relative movement between portions of a reservoir establish a set volume of medication for delivery. The delivery device may include a nosepiece for fitting into the nostril of the user or patient, a medication or drug reservoir or dosing chamber, and an external reservoir adapter for providing the medication from an external reservoir.

12 Claims, 7 Drawing Sheets

(51) Int. Cl.
*A61M 11/02* (2006.01)
*A61M 15/00* (2006.01)

(52) U.S. Cl.
CPC .... *A61M 15/0013* (2014.02); *A61M 15/0025* (2014.02); *A61M 15/0035* (2014.02); *A61M 15/0066* (2014.02); *A61M 15/009* (2013.01); *A61M 2205/273* (2013.01); *A61M 2210/0618* (2013.01)

(58) Field of Classification Search
CPC .. A61M 11/002; A61M 11/02; A61M 15/009; A61M 2205/273; A61M 2210/0618; A61M 5/31551; A61M 2202/0468; A61M 2205/583; A61M 15/0036; A61M 15/004; A61M 11/007; B05B 11/0054; B05B 11/3007

See application file for complete search history.

(56) References Cited

U.S. PATENT DOCUMENTS

| | | |
|---|---|---|
| 5,413,255 A | 5/1995 | Dent |
| 5,423,752 A | 6/1995 | Haber |
| 2004/0094146 A1 | 5/2004 | Schiewe et al. |
| 2005/0209554 A1 | 9/2005 | Landau |
| 2008/0210228 A1 | 9/2008 | Corbacho |
| 2008/0210229 A1 | 9/2008 | Corbacho |
| 2013/0056888 A1* | 3/2013 | Holakovsky |
| 2015/0040890 A1 | 2/2015 | Besseler |
| 2015/0100017 A1 | 4/2015 | Knight et al. |
| 2015/0122257 A1* | 5/2015 | Winkler ............ A61M 16/109 128/203.15 |
| 2020/0001017 A1* | 1/2020 | Smith ................ A61M 5/31511 |

FOREIGN PATENT DOCUMENTS

| | | |
|---|---|---|
| WO | 2009086009 A1 | 7/2009 |
| WO | 20120119262 A1 | 9/2012 |

OTHER PUBLICATIONS

European Patent Office; Extended Search Report for corresponding EP Application No. 2081231.4; dated Jun. 10, 2022; 19 pages; Munich, DE.

* cited by examiner

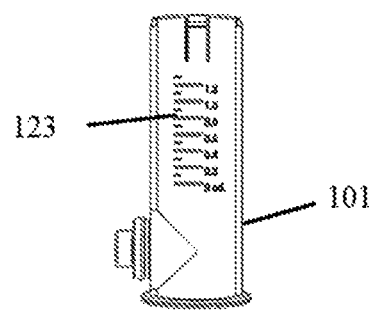
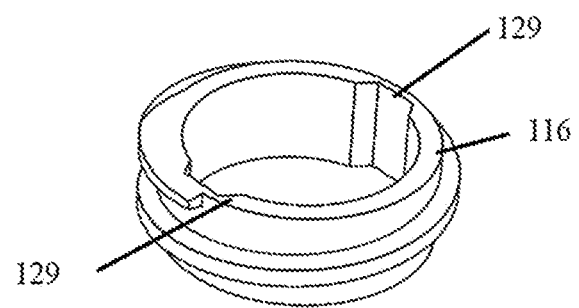
FIG. 5B    FIG. 5C
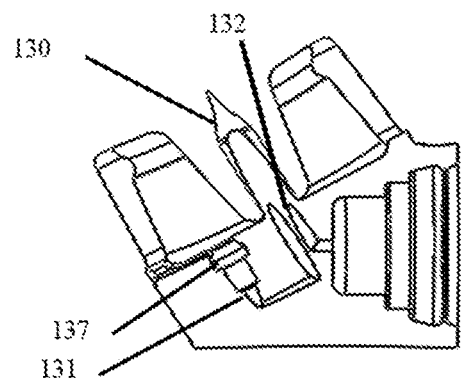
FIG. 6

NASAL MEDICATION OR DRUG DELIVERY DEVICES AND METHODS

RELATED APPLICATIONS

This application claims priority to U.S. provisional application Ser. No. 62/865,783 filed on Jun. 24, 2019 and titled "NASAL MEDICATION OR DRUG DELIVERY DEVICES AND METHODS", which is incorporated herein in its entirety by reference.

BACKGROUND INFORMATION

Current nasal medication or drug delivery devices may exhibit limitations and disadvantages related to controlling dose, such as containing only pre-inserted medication or requiring the use of a syringe for extracting a portion of the medication from the container or vial for providing a set metered dose, requiring the use of specific medication containers, or requiring exchange of the medication container. Although these devices may supply the user with a metered drug dose, these can pose a needle-stick risk and are generally medication-specific and dose-specific. Such delivery systems generally do not provide for adjustment or selection of the metered dose nor a solution for universal adaptation for different doses, medications, or medication containers. Such delivery systems also generally only provide a single nozzle/tip for all users instead of multiple optimally-designed nozzles for different users, doses, or medications, and some do not offer delivery of the desired nasal medication or drug in multiple user orientations.

FIELD OF THE INVENTION

The field of the invention generally relates to nasal medication or drug delivery devices, systems, and methods and, more particularly, to nasal medication or drug delivery devices, systems, and methods adapted to provide different metered volumes or doses.

DESCRIPTION OF THE RELATED ART

Current nasal medication or drug delivery devices deliver medication or drugs to the nasal passages through the expulsion and atomization of liquids. Nasal spray bottles currently available are able to deliver multiple doses of one pre-set fixed volume. The MAD Atomizer by Teleflex, Inc., for example, allows the user to set a metered dose by withdrawing or extracting the medication from a vial using a syringe. Similar devices like the NARCAN nasal spray offered by Teva Pharmaceutical Industries Ltd. only deliver one single dose per device. Moreover, most of these devices include a single nozzle for positioning in or in close proximity to the nasal passageway. Accordingly, improvements are sought in providing adjustability or selectability of metered doses of various medications.

SUMMARY

In accordance with embodiments of the invention, improved nasal medication or drug delivery devices, systems, and methods advantageously provide for the user/patient to adjust, select, or otherwise set a metered dose or volume for delivery. In accordance with other embodiments of the invention, improved nasal medication or drug delivery devices and methods advantageously provide for broad adaptation to accommodation of different medication or drug containers, bottles, vessels, or vials (these and other medication containers are referred to herein as "vials"). In accordance with further embodiments of the invention, improved nasal medication or drug delivery devices and methods advantageously include the ability to use multiple interchangeable nozzle tips optimally designed for different users. In accordance with yet other embodiments of the invention, improved nasal medication or drug delivery devices and methods may allow use in multiple user or patient orientations. In accordance with yet other embodiments of the invention, improved nasal medication or drug delivery devices and methods may allow the administrator to avoid a high risk of needle-stick.

One aspect of the invention features, in some embodiments, a nasal delivery device for delivering a medication or drug to a nasal passageway in a metered amount. The device includes a connection adapter having a receiving portion comprising a puncturing member and one or more sealing members presented on the connection adapter. The device includes a first chamber presenting a metered amount indicator and being fluidly coupled to the connection adapter; and a second chamber having a fluid atomizing tip, the second chamber fluidly coupled to the first chamber, and the second chamber being movable relative to the first chamber to a set position along the metered amount indicator to thereby establish a selected metered dose volume jointly defined by the first chamber and the second chamber.

In some embodiments, the nasal delivery device includes a positive displacement mechanism for moving liquid from at least a first external reservoir to at least one of the first and second chambers. In some embodiments, the nasal delivery device includes a moveable mechanism coupled to at least one of the first chamber and the second chamber for adjustment of the metered dose volume. In some embodiments, the nasal delivery device includes a universal adapter for the attachment of different vials. In some embodiments, the nasal delivery device is configured to allow for particle separation of a liquid substance in specific target particle size.

In some embodiments, the nasal delivery device includes at least one anti-backflow membrane preventing backflow of liquids into the at least first chamber or from an external source into the at least first chamber or the second chamber. In some embodiments, at least the first chamber is fluidly connected to the second chamber allowing for free rotation and positioning of the at least first chamber with respect to the second chamber while maintaining a liquid seal therebetween.

In some embodiments, the nasal delivery device includes a puncture and seal mechanism for the attachment and extraction of liquid from one external reservoir to the at least first chamber within the device. In some embodiments, the nasal delivery device includes at least one disposable protective cap for preventing the contamination of medication or a drug contained within the device. In some embodiments, the nasal delivery device is configured to separately receive multiple different nozzle attachments. In some embodiments, the nasal delivery device is configured for at least one of single-use disposable and multiple uses.

Another aspect of the invention features, in some embodiments, a nasal delivery device including at least one chamber fluidly connected to a second chamber with a rotatable mechanism disposed between the first and second chambers configured for adjusting a fluid displacement volume jointly defined by the first and second chambers.

In some embodiments, the nasal delivery device includes a spring plunger. In some embodiments, the nasal delivery device includes volumetric indicators along at least one of the first and second chambers. In some embodiments, a rotatable mechanism is configured for selection among pre-set locking positions for specific volume increments defined by the first and second chambers.

In some embodiments, the nasal delivery device includes a spring plunger mechanism including an anti-rotation locking mechanism.

Another aspect of the invention features, in some embodiments, a nasal dose delivery device including first and second telescoping dose container chamber portions configured to rotatably telescope to establish a selected dose volume and being further configured to slidingly telescope to deliver the selected dose volume.

In some embodiments, the nasal delivery device includes a threaded slider ring interposed between the first and second telescoping dose container chamber portions and configured such that relative rotation between the first and second telescoping dose container chamber portions adjusts a dose volume jointly defined by the first and second telescoping dose container chamber portions and wherein the threaded slider ring is further configured to be lockable in a first position during relative rotation between the first and second telescoping dose container chamber portions and unlockable to allow telescopic sliding between the first and second telescoping dose container chamber portions to deliver the selected dose volume.

In some embodiments, the nasal delivery device includes a vial piercer in fluid communication with the first and second telescoping dose container chamber portions to fill the selected dose volume with medicine from a vial. In some embodiments, the nasal delivery device is configured for attachment of multiple vials for titration of multiple substances prior to delivery.

Another aspect of the invention features, in some embodiments, an improved nasal medication or drug delivery device including: (1) at least one fluid or liquid chamber/reservoir fluidly connected or coupled to another chamber/reservoir, allowing for the free rotation and positioning of one chamber/reservoir with respect to the delivery device and to the other chamber/reservoir while maintaining a liquid seal between the chambers/reservoirs; (2) a puncture and seal mechanism for attachment and extraction of liquid from an external reservoir to a chamber/reservoir of the delivery device. In some embodiments, multiple nozzle pieces or nosepieces may be exchanged and attached to the delivery device. In some embodiments, the delivery device is a single use or multiple use design.

In some embodiments, the at least one chamber/reservoir is fluidly connected or coupled to another chamber/reservoir with a rotating mechanism for adjusting volume and/or fluid displacement in one or both chambers/reservoirs. In some embodiments, the at least one chamber/reservoir is fluidly connected or coupled to another chamber/reservoir containing a spring plunger. In some embodiments, the at least one chamber/reservoir is fluidly connected or coupled to another chamber/reservoir with volumetric indicators for the chamber/reservoir volume. In some embodiments, the at least one chamber/reservoir is fluidly connected or coupled to another chamber/reservoir having pre-set locking positions for specific volume increments. In some embodiments, the at least one chamber/reservoir is fluidly connected or coupled to another chamber/reservoir containing a spring plunger mechanism having an anti-rotation mechanism.

BRIEF DESCRIPTION OF THE DRAWINGS

FIG. 5B show plan views of the first chamber of the nasal medication or drug delivery device of FIG. 1.

FIG. 5C shows a perspective view of a fixing member of the nasal medication or drug delivery device of FIG. 1.

FIG. 6 shows a cross-sectional view of a universal container adapter or connector adapter of the nasal medication or drug delivery device of FIG. 1.

DETAILED DESCRIPTION OF THE INVENTION

Figure 1:
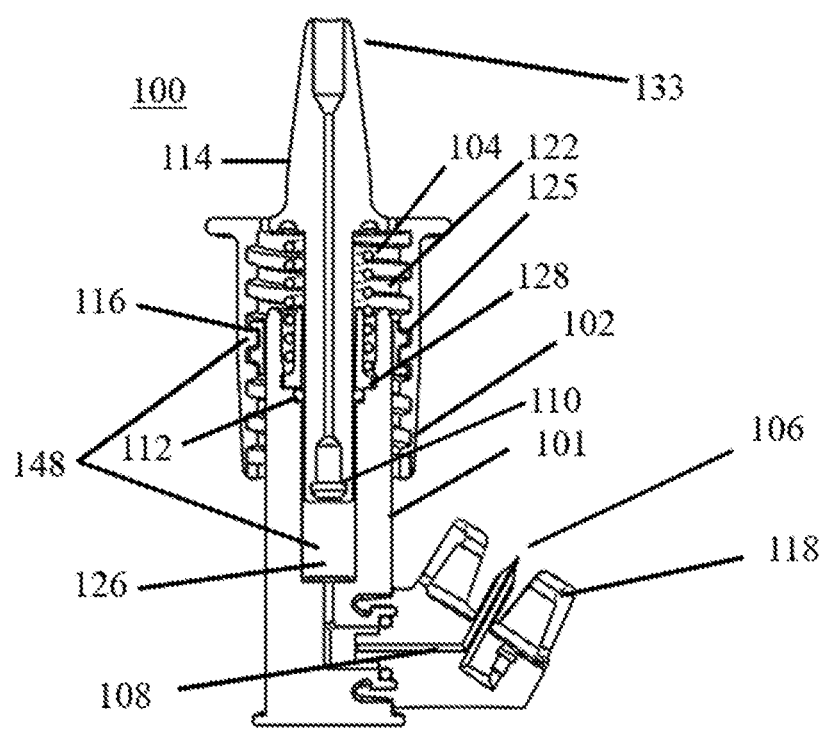
FIG. 1 schematically shows a perspective, partial cross-sectional view of a nasal medication or drug delivery device, in accordance with an embodiment of the invention.
Figures 5, 5A:
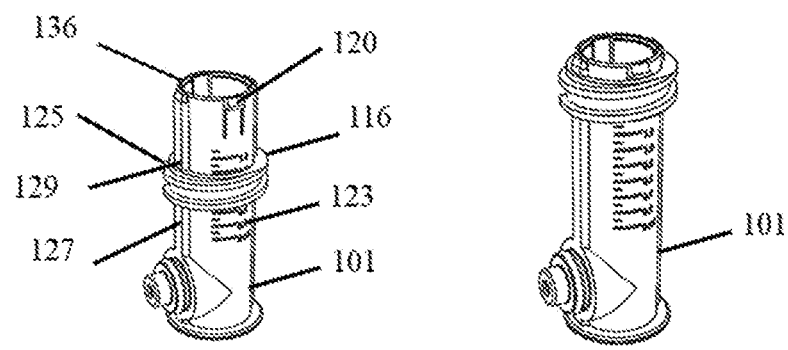
FIGS. 5 and 5A show perspective views of a first chamber and a fixing member of the nasal medication or drug delivery device of FIG. 1.

With reference to FIG. 1, in accordance with an embodiment of the invention, a nasal medication or drug delivery device 100 includes an inner hollow chamber 101, an outer hollow chamber 102 having threads 122, a compression spring 104, a vial or container adapter 106, a first one-way valve or check valve 108, such as a duckbill valve, a second one-way valve or check valve 110, such as a duckbill valve, and a sealing member 112, such as an O-ring seal. A nose cone or nosepiece 114 is formed integral with or attached to outer chamber 102. A slidable fixing member 116, such as a threaded nut, and flexible locking tabs 120 (see FIGS. 3 and 5), e.g., cantilevered snap-fit tabs, serve to fix the position of chambers 101 and 102. Various components discussed herein may be constructed of biocompatible materials, such as medical grade polyvinyl chloride (PVC), high density polyethylene (HDPE), polyethylene, polyetheretherketone (PEEK), or the like. The "chamber" as used herein, means complimentary portions of a container, such as two cylinders telescopingly engaged to form variable volume container. The term chamber can include any geometry of complementary container portions suitable to establish a variable container volume for use in delivery of metered dose volumes.

In some embodiments, nose cone 114 may include a disposable nose cone cover or cap useful for preventing the contamination of the medication or drugs contained within delivery device 100 and/or may include a foam nose cone bumper (not shown) that fits over an end of nose cone 114 to be inserted into the nasal passageway that may be anthropomorphically adapted for specific recipient populations of certain ages or weights with unique nasal passage shapes or sizes. A foam nose cone bumper may be made of a soft material for purposes of sealing and may be sized to preventing deep insertion into the nasal passageway for safety. Nose cone 114 itself may be configure with an integral nose cone bumper for the same purposes. Moreover, in some embodiments, nose cone 114 and/or outer chamber 102 may be varied for use with multiple interchangeable nozzle tips optimally designed for different users or patients of different ages and weights or with unique nasal passage shapes. In yet other embodiments, nose cone 114 may be detachable and re-attachable from the rest of outer chamber 102 and may have different shapes and/or sizes or different outer chambers 102 may have nose cones 114 having different shapes and sizes for different users or patients.

The various components of delivery device 100, e.g., locking tabs 120, fixing member 116, outer chamber 102, etc., may be formed from any suitable material using any suitable process and assembled into a functional device or system. Delivery device 100 then may be employed by a user or patient to advantageously delivery medication or drugs inside the user or patient's the nasal cavity.

Figure 2:
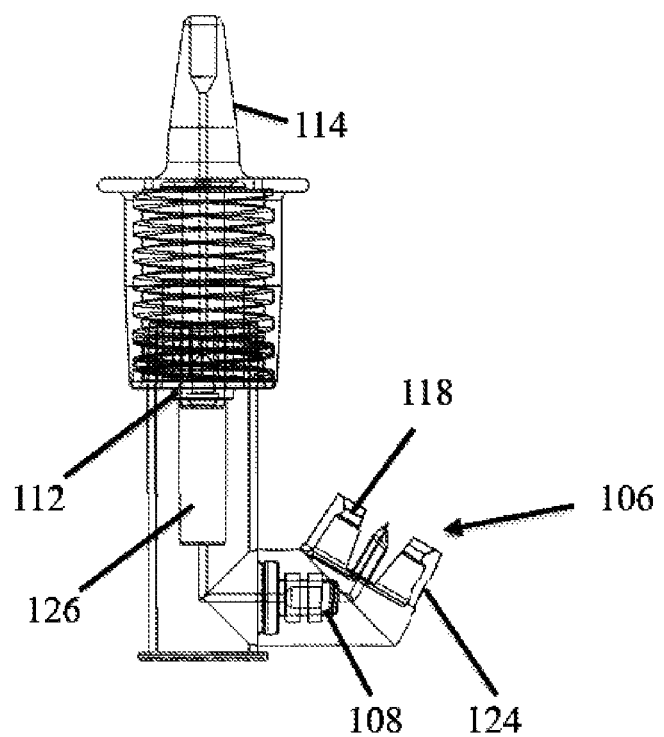
FIG. 2 shows a cross-sectional view of a portion of the nasal medication or drug delivery device of FIG. 1.
Figure 2A:
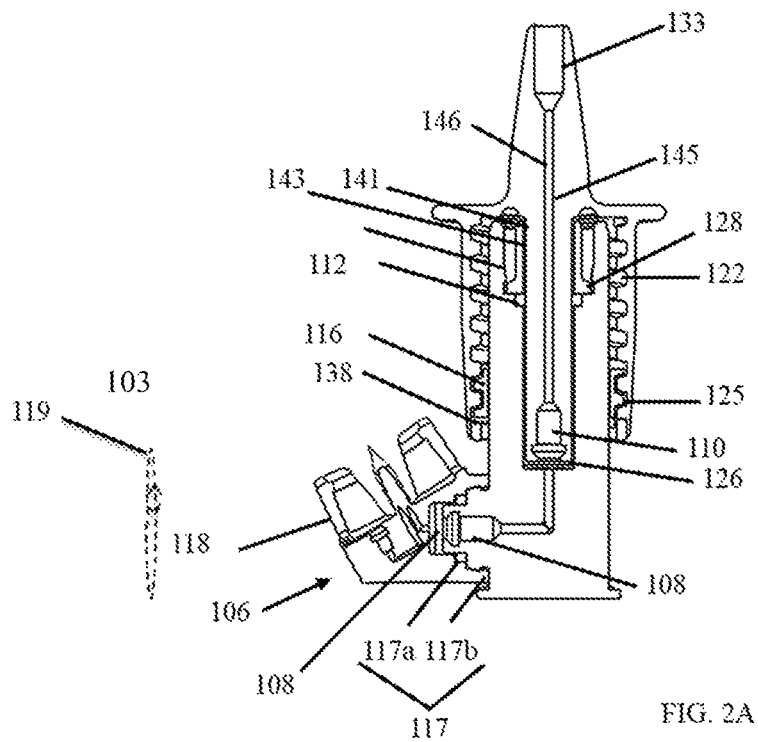
FIG. 2A shows a cross-sectional view of a portion of the dosing chamber with a universal connector adapter of FIG. 1.

Valves 108 and 110, which may be one-way check valves, such as duckbill valves, as shown in more detail in FIG. 2A, are fluidly coupled together and to adapter 106 to work to provide dual-positive-displacement valve operation. In some embodiments, valves 108 and 110 work together to allow airflow for priming only in one direction (e.g., from a fluid volume reservoir or chamber and then out nose cone 114) and fluid flow also only in one direction (e.g., from a medical or drug vial or reservoir toward the fluid volume reservoir or chamber and then out nose cone 114) through the combination of the valves with no or little, if any, backflow of air or fluid. A fluid volume chamber 126 and a plunger 103 (see FIG. 3), for example, a spring driven plunger or spring plunger, disposed within delivery device 100, along with one-way check valves 108 and 110, form a positive displacement pump for moving liquid from at least one supply reservoir (the vial) to another reservoir (chamber 126), as described below. In certain other embodiments, any or all of valves 108 and 110, as well as a valve 137 (described below), may be valve and membrane combinations that provide a similar anti-backflow function as do duckbill valves.

Vial connector adapter 106 ("connector adapter") may be a universal connector adapter for a variety of commonly used containers, reservoirs or vials. Connector adapter 106 incorporates a cylindrical container or vial connector 117 that includes, for example, an annular press-fit or snap-fit connector 117a and a sealing member 117b, such as an O-ring, as shown in FIG. 2A, which forms a dynamic radial seal to the inner chamber 101 to prevent or at least reduce the likelihood of fluid leakage once a typical medication or drug container or vial is connected (see FIG. 4). Connector 117 allows for rotation at its annular portion 124 (see FIG. 2) in the rotational directions schematically indicated by the hashed perspective circular arrow 119 in FIG. 2A. This rotation is about an imaginary longitudinal axis (not shown) in the center of and perpendicular to the plane of sealing member 117b while the sealing function is maintained. This allows the attached vial and inner chamber 101 to be rotated relative to each other such that the vial may be maintained in a generally vertically aligned and upside-down position, as in FIG. 4, no matter whether the user or patient is standing, sitting, or lying prone, for example.

Figure 4:
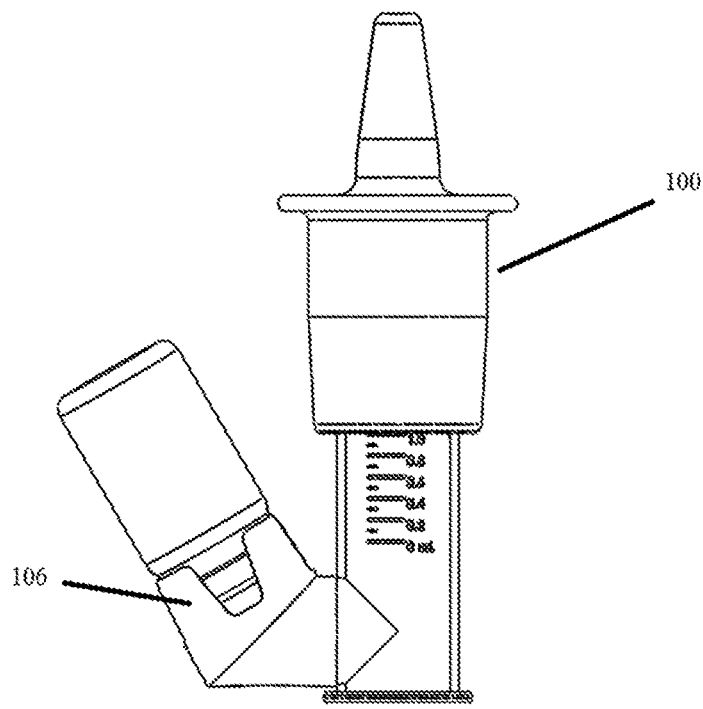
FIG. 4 shows a plan view of a typical medication or drug container or vial attached to the nasal medication or drug delivery device of FIG. 1.

In certain embodiments, the press-fit or snap-fit connector 117 may include components or structures, such as a ratcheting mechanism, that allow the rotational position or angle of the annular portion of connector 117 relative to inner chamber 101 to be locked or secured in discrete rotational positions, for example, by using rotational orientation markers on connector 117 and/or on the lower components of inner chamber 101 that mate with connector 117. Such a mechanism may be used to align the vial generally vertically as shown in FIG. 4 to prevent rotation of the attached vial when the user or patient is using delivery device 100 to pump the medication or drugs into the nasal passageways. The ratcheting mechanism may be released and relocked for setting another rotational position to adjust the vial to be generally aligned vertically and upside down when needed, for example, if the user or patient changes their position. This mechanism serves to prevent air from being forced into the fluid volume chamber 126 (described below) of the delivery device 100 from the vial when filling the chamber 126 or to prevent air from being pumped into the nasal passageway.

In certain other embodiments, the press- or snap-fit connector 117, which receives and mates to the lower components of inner chamber 101 during assembly by pushing these lower components into connector 117 (see FIG. 2A), is not used. Instead, a cantilevered press-fit or snap-fit connector may be used (not shown). In these embodiments, components of this cantilevered press-fit or snap-fit connector are part of and assembled with a different vial connector that connects to a different inner chamber by pushing the cantilevered connector into a lower receiving and mating portion of this inner chamber.

Connector adapter 106 may include vial receiving protrusions having flexible tapered clips 118, as shown in FIGS. 1, 2, and 2A. Clips 118 are flexible enough to allow for their expansion over a top rim of the vial to help securely fix and hold the vial in place in connector adapter 106, such as in FIG. 4. Tapered outer clips 118 are useful for reproducibly latching and controlling the depth of the vial in connector adapter 106.

FIG. 6 shows a vial puncture mechanism of connector adapter 106 that may be used when a vial is attached in adapter 106. The puncture mechanism includes, for example, a hollow puncturing needle 130 that punctures the vial's seal. The Needle 130 is preferable designed with height shorter than the vial adapter to reduce needle stick and safety concerns.

Needle 130 includes an air supplying channel 131 and a medication or drug supplying channel 132. Air supplying channel 131 provides external air through the one-way check valve 137, such as a duckbill valve, into the seated and punctured vial to prevent, or at least reduce the likelihood of, fluid backflowing from the vial into air supplying channel 131. Medication or drug supplying channel 132 provides the medication or drug when drawn (and thus reducing/adjusting the volume of fluid in the vial) into the volume chamber 126 of delivery device 100 via negative pressure, such as when delivery device 100 is being primed for use. Air supplying channel 131 may be used to equilibrate the pressure in the vial as medication or drug fluid is being drawn into delivery device 100.

FIGS. 2 and 2A show how outer chamber 102, fixing member 116, and inner chamber 101 of delivery device 100 are connected, coupled, or joined with tight tolerance. For example, threads 122 of outer chamber 102 may join to corresponding mating threads 125 of fixing member 116, which is positioned over and makes sliding contact with inner chamber 101, as shown in FIGS. 2, 2A, 5, 5A, and 5C. Threads 122 allow outer chamber 102 to be rotated clockwise or counterclockwise (from a view looking down on nose cone 114, as would be understood by one of ordinary skill in the art) with respect to threads 125 of fixing member 116 to which they are mated. Outer chamber 102 may be adjusted vertically in this manner with respect to inner chamber 101, such that rotation of outer chamber 102 may be used to change the volume of chamber 126 to set a specific volume of medication or drug fluid 105 to be atomized during use, which will be described further below. Fixing member 116 also includes cut out sections, portions, or grooves 129 on its interior circular opening that fits over rails, slides, or guides 127 of interior chamber 101, which allow sliding vertical motion of fixing member 116 up and down along guides 127 with respect to inner chamber 101 and serves to prevent or limit rotational motion of fixing member 116 with respect to inner chamber 101 as volume is set or during administration of medication or drugs. Over a range of volume settings, spring 104 is biased to keep the top of fixing member 116 positioned against locking tabs 120 before the user or patient presses the flange or tab 109 (shown in FIGS. 3 and 7) for administration. Spring 104 is compressed from its most relaxed or resting position when smaller volumes than the maximum volume are being set (see FIG. 7), as will be described below. During administration, the fixing member moves down inner chamber 101 away from locking tabs 120. The maximum vertical position of outer chamber 102 with respect to inner chamber 101 is determined by unscrewing outer chamber 102 from fixing member 116 until fixing member 116 is captured between a bottom part of the threads or bottom end 138 (See FIG. 2A) of outer chamber 102 and tabs 120 without the user or patient pressing flange or tab 109 and spring 104 is in its most resting and relaxed state. The minimum vertical position of outer chamber 102 with respect to inner chamber 101 is determined by screwing outer chamber 102 onto fixing member 116 until the underside of flange or tab 109 of outer chamber 102 makes contact with tabs 120 and top rim surface 136 of inner chamber 101 shown in FIG. 5.

FIG. 2A illustrates the structure of plunger 103 of outer chamber 102. Plunger 103 (driven by spring 104, thus forming a spring plunger) includes one-way check valve 110, a hollow rod 145, and the atomizing tip 133, which are located or disposed within a hollow portion or channel 146 of outer chamber 102 in assembling delivery device 100. Valve 110 and atomizing tip 133 are press-fitted into hollow portion or channel 146 with hollow rod 145 disposed in between. These components are in mechanical and fluid cooperative communication with each other in order to function as part of pump and fluid atomizing mechanisms to spray the medication or drug into the nasal passageway from fluid chamber 126.

Figures 3, 3A:
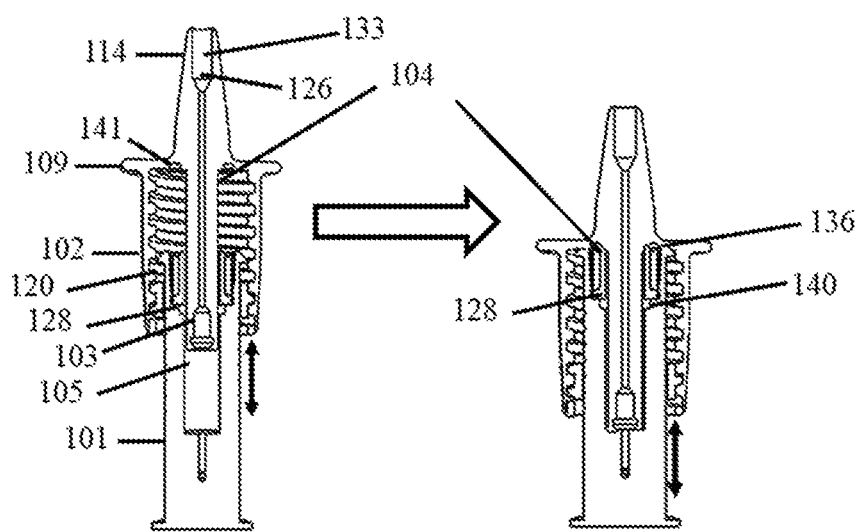
FIGS. 3 and 3A schematically show cross-sectional views of a portion of the nasal medication or drug delivery device of FIG. 1; before activation (FIG. 3) and upon activation (FIG. 3A) of a pumping mechanism for releasing a spray of fluid into a nasal passageway, in accordance with an embodiment of the invention.

FIG. 2A with FIGS. 3 and 3A illustrate how plunger 103 and pumping action operate. Valves 108 and 110 work together to fill and prime delivery device 100 as follows. To evacuate air from fluid chamber 126 without or reducing the likelihood of drawing fluid into chamber 126 from the fluid container or vial, the user or patient presses on flange or tab 109. This action pushes plunger 103 down into chamber 126 with valve 110 open and valve 108 closed, which applies positive pressure to the air in chamber 126 and forces the air out through plunger 103 to be expelled from tip 133. Fluid is prevented from entering chamber 126 from the vial or at least very minimized because valve 108 is closed in this instance. Then user or patient then stops pressing flange or tab 109 and spring 104 forces outer chamber 102 and plunger 103 up and away from chamber 126. While this upward motion occurs, valve 110 is closed and valve 108 is open. This results in a negative pressure being applied to the fluid in the vial to fill chamber 126. These actions may have to be repeated to fully prime delivery device 100 to the set amount or metered volume of fluid in chamber 126 for subsequent administration by the user or patient. To deliver the atomized fluid to the user or patient, they may simply press flange or tab 109 of primed delivery device 100 or metered pump the metered volume of fluid from chamber 126 up through plunger 103 and out atomizing tip 133 with valve 110 open and valve 108 closed, as above.

Figure 3B:
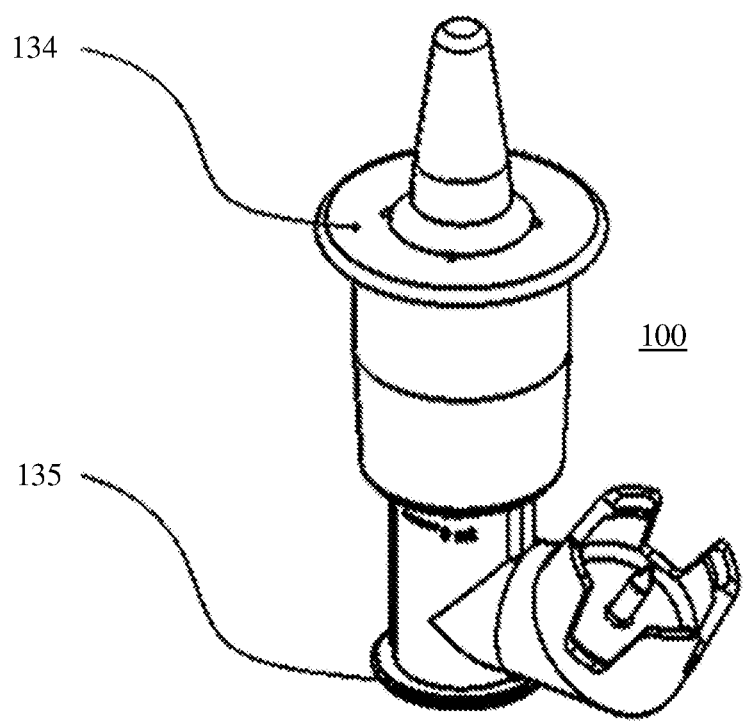
FIG. 3B shows a perspective view of the nasal medication or drug delivery device of FIG. 1 indicating finger and thumb placement locations for activation of the pumping mechanism.

Referring to FIGS. 1, 3, and 3A, outer chamber 102 is designed to fit and move along with fixing member 116 over inner chamber 101 when flange or tab 109 is pressed, which causes plunger 103 to apply pressure to the fluid in chamber 126 to dispense atomized fluid from tip 133. Outer chamber 102 is in contact with spring 104 attached to inner chamber 101. That contact is made with one end of spring 104 held in place by a keeper groove, cylindrical, or circular channel 141 located within the interior of nose cone 114 of outer chamber 102. The other or opposite end of spring 104 bears against a cylindrical collar 128 disposed or positioned between an inner portion 142 of outer chamber 102 and an inner portion 143 of inner chamber 101, as shown in FIG. 2A, in assembled delivery device 100. Sealing member 112 serves to prevent or reduce the likelihood of leakage of fluid from chamber 126 and is positioned and held in place to do so between cylindrical collar 128 and inner chamber 101, as shown in FIGS. 2, 2A, 3, and 3A. The left side of FIG. 3 shows delivery device 100 with spring 104 in a rest or its most relaxed state, that is, uncompressed or in its least compressed state, and fluid 105 in chamber 126. FIG. 3A shows delivery device 100 when a user or patient has pressed flange or tab 109 of nose cone 114 with their fingers, for example, as shown in FIG. 3B with a finger at location 134 and thumb at location 135, to activate the pumping mechanism to administer a dose of fluid 105, as described above.

The action of pressing tab 109 compresses spring 104, which causes outer chamber 102 to slide over inner chamber 101 and plunger 103 to force fluid 105 to move through nose cone 114 for atomization. This action empties or reduces the volume of fluid 105 in chamber 126, as shown by comparing FIG. 3 with FIG. 3A. The arrows in FIGS. 3 and 3A show the relative direction of motion of spring 104, outer chamber 102, and plunger 103 with respect to inner chamber 101 before and during the compression action.

When priming device 100 or pumping medication or drugs, the extent of travel of outer chamber 102 down along inner chamber 101 is checked or stopped, as shown in FIG. 3A, by the upper circular portion or rim 136 of inner chamber 101 making contact with the underside of the flange or tab 109. Certain embodiments of the invention may include an anti-rotation mechanism or structures and/or components (not shown) that prevent rotation of the outer chamber 102 relative to fixing member 116, which may cause administration or other problems during activation of plunger 103 by the user or patient to prime or pump medication or drugs to the nasal passageway. In certain other embodiments, an anti-rotation mechanism or structures and/or components (not shown) may be included to prevent rotation of the spring plunger for the same reason.

FIGS. 3 and 3A also show atomizing nose cone 114 for insertion into the nasal cavity of the user or patient. The structure of nose cone 114, including its length, shape, and diameter, are important to its function to fit in the user or patient's nasal cavity and to atomize the flow of the fluid 105 into the user or patient's nasal passage. Nose cone 114 may include inner channels (not shown) in tip 133 for forced flow of medication or drug fluid in a spiral pattern to increase the fluid particle or drop velocity for promoting atomization. These inner channels and other associated internal structures have a specific structure(s) for this purpose, including length(s), diameter(s), and geometric shape(s) to generate the needed or target fluid particle or drop velocity, separation, size, spiraling or swirling motion, cone angle and/or pattern of the atomized spray of the fluid exiting delivery device 100 during administration.

Figure 7:
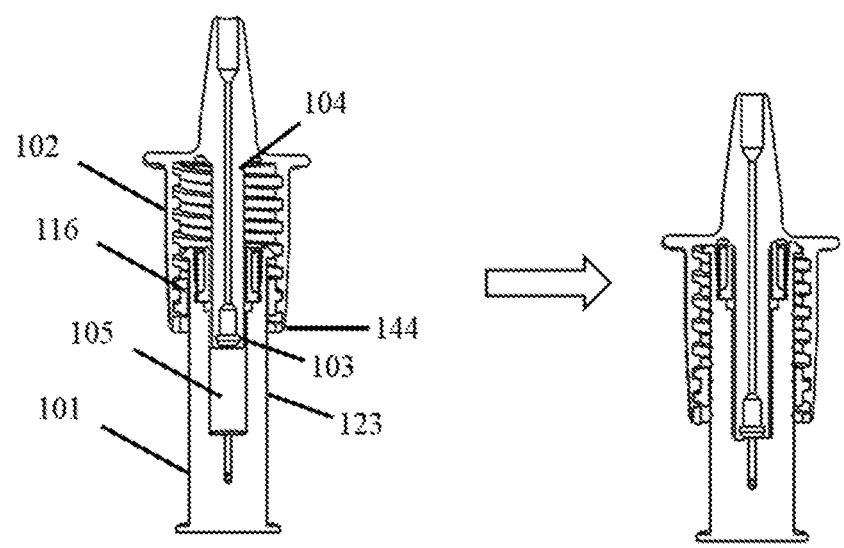
FIG. 7 schematically shows a cutaway view of a portion of the nasal medication or drug delivery device of FIG. 1 set to two different fluid volumes after rotating a second chamber of the nasal medication or drug delivery device about the fixing member, in accordance with an embodiment of the invention.

Referring to FIGS. 1, 2A, and 7, outer chamber 102, with its nose cone 114, may be mechanically and rotatably moved vertically up or down relative to fixing member 116 and inner chamber 101 via internal threads 122 of fixing member 116 that correspond to and mate with threads 125 of fixing member 116. Rotating outer chamber 102 rotates or screws threads 122 on threads 125 of non-rotating fixing member 116. This rotation may be used to set the amount or volume of the medication or drug that will be drawn into the medication or drug volume reservoir from the vial, which, along with plunger 103, forms chamber 126. The user or patient may set a volume in chamber 126 by rotating outer chamber 102 to line up a bottom 144 of outer chamber 102 (see FIGS. 5 and 7) with measured, calibrated, or metered numerical chamber dosage or volume indicators, such as a dosage or volumetric scale or grid 123 formed as part of, inscribed on, or otherwise attached to inner chamber 101. It should be noted that in certain embodiments, a pre-set locking mechanism may be provided for positions of outer chamber 102 relative to indicator 123 when setting specific volumes or volume increments to prevent rotation of the outer chamber 102, for example, during administration. The left side of FIG. 7 shows the volume of chamber 126 set to the maximum value by rotating outer chamber 102 to unscrew threads 122 from threads 125 of fixing member 116 until fixing member 116 is sandwiched between the bottom threaded end 138 of outer chamber 102 and tabs 120. Spring 104 also will be in its corresponding resting or most relaxed state. The right side of FIG. 7 shows the volume of chamber 126 when set to a smaller value after rotating outer chamber 102 in the opposite direction to screw threads 122 onto/along threads 125 of fixing member 116 and lining up the bottom 144 of outer chamber 102 with the chosen volume set point on indicator 123. An exemplary smaller increment for the volume or dosage scale of indicator 123 may be 0.2 mL with a maximum volume or dosage of 1.2 mL also indicated. For volume or dosage that is set less than the maximum, fixing member 116 need not touch tabs 120 and may be positioned along threads 122 of outer chamber 102, as shown on the right side of FIG. 7. Spring 104 also correspondingly will be in between its resting or most relaxed state and its most compressed state. When flange or tab 109 is pressed for the pumping action, spring 104 will reach its most compressed state when flange or tab 109 contacts rim 136.

As described above, during priming or administration, flange or tab 109 is pressed to pump air with or without the fluid through plunger 103 to be expelled from delivery device 100. The volume of fluid in chamber 126 along with activation of the plunger from the user or patient's finger press on flange or tab 109 may determine the actual dose or volume of the medication or drug delivered during one or more strokes or pumps of plunger 103. During the pumping action, fixing member 116 slides down along guides 127, spring 104 compresses further, and plunger 103 moves down against the volume of fluid whose volume had been set and then drawn into chamber 126. When the user or patient releases flange or tab 109, fixing member 116 moves back up guides 127 until it makes contact with tabs 120 and the spring decompresses to its resting or most relaxed vertical state or position.

The changeable volume or dose setting 148 produces a corresponding changeable increase or decrease in pressure while outer chamber 102 of delivery device 100 is rotated. Rotation to move outer chamber 102 down along inner chamber 101 will push air or fluid out of delivery device 100 with positive pressure. Rotating it up will draw the medication or drug from an attached vial into chamber 126. The dose or volume 148 depends on the relative position of outer chamber 102 to fixing member 116 and to the volume set by outer chamber 102 on the measured, calibrated, or metered numerical chamber dosage or volume indicators 123. The volume indicators 123 can be configured as a guide indicator for the user to determine the correct dose per medication or patient.

In some embodiments, a syringe plunger is configured with a conical shape for creating a fluid liquid seal with the need to use sealing O-rings. In some embodiments, the components are configured to be assembled by press-fit or snap-fit attachment for quick and easy assembly.

In some embodiments, a 360 degree rotating connector adapter allows for universal orientation drug delivery (vertical or horizontal patients). In some embodiments, the device includes ergonomic outer grip features and designs to aid and instruct the user for proper and secure holding of the device.

In some embodiments, the nasal drug delivery device allows for attachment of multiple vials for automatic titration of multiple substances while administering, e.g., where one vial may be a drug and the other vial may be a diluting agent where the device allows for the mixing of the drugs prior to delivery.

In some embodiments, the device includes interchangeable atomization tips for delivering different particle sizes specific for different drugs. Interchangeable tips allow for delivery of different compound forms as in foam or gel substance.

In some embodiments, a rotating connector adapter with set locking positions with indicators based on target patient orientation.

In some embodiments, an atraumatic nose cone design is configured to prevent trauma to patient. In some embodiments, interchangeable nose cones are provided for different size patients (i.e. pediatric versus adult patients.)

It should be understood that delivery device 100 described herein may be single use or multi-use, depending on the embodiment. It also should be understood that all of the components of delivery device 100 through which the medication or drug fluid flows or moves are mechanically and fluidly cooperatively connected, coupled, or in communication, whether direct or indirect.

The specific embodiments described above are merely exemplary, and it should be understood that these embodiments may be susceptible to various modifications and alternative forms. Any structures, components, or process parameters, or sequences of steps described and/or illustrated herein are given by way of example only and can be varied as desired. For example, for any steps illustrated and/or described herein that are shown or discussed in a particular order, these steps do not necessarily need to be performed in the order illustrated or discussed. The various exemplary embodiments that include structures, components, or methods described and/or illustrated herein may also omit one or more of such structures, components, or steps described or illustrated herein or include additional structures, components, or steps in addition to those disclosed. It should be further understood that the claims are not intended to be limited to the particular embodiments or forms disclosed, but rather to cover all modifications, equivalents, and alternatives falling within the spirit and scope of this disclosure.

What is claimed is:

1. A nasal delivery device for delivering a medication or drug to a nasal passageway in a metered amount, comprising: a connection adapter having a receiving portion comprising a puncturing member; one or more sealing members presented on the connection adapter; a first chamber portion, comprising a first chamber, presenting a metered amount indicator and being fluidly coupled to the connection adapter; and a second chamber portion, comprising a second chamber, having a fluid atomizing tip, the second chamber fluidly coupled to the first chamber, and the second chamber allowing for free movement and positioning relative to the first chamber to a set position along the metered amount indicator to thereby establish a selected metered dose volume jointly defined by the first chamber and the second chamber; while maintaining a liquid seal therebetween.

2. The nasal delivery device of claim 1 further comprising a positive displacement mechanism for moving liquid from at least a first external reservoir to at least one of the first and second chambers.

3. The nasal delivery device of claim 1 further comprising a universal adapter for the attachment of different vials.

4. The nasal delivery device of claim 1 configured for movement of at least one of the first chamber and the second chamber for adjustment of the metered dose volume.

5. The nasal delivery device of claim 1 further configured to allow for particle separation of a liquid substance in specific target particle size.

6. The nasal delivery device of claim 1 further comprising at least one anti-backflow membrane preventing backflow of liquids into the at least first chamber or from an external source into the at least first chamber or the second chamber.

7. The nasal delivery device of claim 1 further comprising a seal puncture mechanism for extraction of liquid from one external reservoir to the at least first chamber within the device.

8. The nasal delivery device of claim 1 configured to separately receive multiple different nose cone attachments.

9. The nasal delivery device of claim 1 designed for at least one of single-use disposable and multiple uses.

10. A nasal dose delivery device comprising first and second telescoping dose container chamber portions configured to rotatably telescope to establish a selected dose volume and being further configured to slidingly telescope to deliver the selected dose volume; and further comprising a threaded slider ring interposed between the first and second telescoping dose container chamber portions and configured such that relative rotation between the first and second telescoping dose container chamber portions adjusts a dose volume jointly defined by the first and second telescoping dose container chamber portions and wherein the threaded slider ring is further configured to be lockable in a first position during relative rotation between the first and second telescoping dose container chamber portions and unlockable to allow telescopic sliding between the first and second telescoping dose container chamber portions to deliver the selected dose volume.

11. The nasal dose delivery device of claim 10, further comprising a 360-degree rotational vial adapter and a vial piercer in fluid communication with the first and second telescoping dose container chamber portions to fill the selected dose volume with medicine from a vial.

12. The nasal dose delivery device of claim 10, configured for attachment of multiple vials for titration of multiple substances prior to delivery.

* * * * *